United States Patent [19]

Luther et al.

[11] Patent Number: 4,612,170

[45] Date of Patent: Sep. 16, 1986

[54] BLOOD OXYGENATOR WITH DUAL SPARGER AND REUSEABLE HEAT EXCHANGER

[76] Inventors: Ronald B. Luther, 530 Kings Rd., Newport Beach, Calif. 92663; Pradip V. Choksi, 10935 Yolanda Ave., Northridge, Calif. 91326

[21] Appl. No.: 503,614

[22] Filed: Jun. 13, 1983

[51] Int. Cl.⁴ ............................................. A61M 1/03
[52] U.S. Cl. .............................. 422/46; 261/DIG. 28
[58] Field of Search ................... 422/46; 261/DIG. 28

[56] References Cited

U.S. PATENT DOCUMENTS

| | | | |
|---|---|---|---|
| 4,160,801 | 7/1979 | Badolato et al. | 261/DIG. 28 X |
| 4,180,896 | 1/1980 | Reed et al. | 422/46 X |
| 4,254,081 | 3/1981 | Streczyn et al. | 422/46 |
| 4,374,088 | 2/1983 | Stenoerg et al. | 422/46 |
| 4,407,777 | 10/1983 | Wilkinson et al. | 422/46 |

Primary Examiner—Frank Spear
Attorney, Agent, or Firm—Willie Krawitz

[57] ABSTRACT

A blood oxygenator providing a removeable and reuseable heat exchanger is constructed from a hollow, aluminum extrusion of circular cross section having integrally formed, external, spirally wound fins.

A dual sparger system is used to supply a combination of $O_2$ and $CO_2$ plus $O_2$ to the blood in different bubble sizes to enhance $O_2$ absorption and $CO_2$ removal.

18 Claims, 5 Drawing Figures

BLOOD OXYGENATOR WITH DUAL SPARGER AND REUSEABLE HEAT EXCHANGER

BACKGROUND OF THE INVENTION

This invention relates to a new and improved blood oxygenator having an improved, reuseable heat exchanger and a dual sparger system for increasing oxygenation efficiency and $CO_2$ removal.

Blood oxygenators are usually designed with the intent of using components that are premanently secured in the device, the principal one being the heat exchanger. This item constitutes one of the major expenses in a blood oxygenator; however, after use, the heat exchanger is usually discarded along with the body of the oxygenator. If the heat exchanger could be readily detached from the blood oxygenator and reused, the cost of the equipment would be reduced considerably. Also, since fewer heat exchangers would be required overall in a particular facility, they could be manufactured to a much higher quality than if they were mass produced. This in turn would reduce the possibility of producing a defective component, and also would reduce quality control costs. A replaceable heat exchanger should be capable of quick and easy removal from the oxygenator and connecting water lines. Also, the movement of cooling water through the heat exchanger should be simple and efficient, and preferably with little opportunity for scale build up.

In the case of a finned heat exchanger, the transfer efficiencies of oxygen will depend on the amount of finned surface available for contact between the blood and the oxygen bubbles. Hence, a heat exchanger configuration having spirally wound fins should increase the residence time for the blood and improve oxygen transfer efficiencies compared to a finned heat exchanger having parallel fins. Similarly, a spirally wound finned heat exchanger is preferred for efficiency of heat exchange.

In U.S. Pat. No. 4,254,081, the inventor herein described an elliptically shaped heat exchanger for a blood oxygenator having spirally wound fins. However, it is not practical to manufacture such a device (as opposed to a heat exchanger having parallel fins) because of severe fin distortion along the major axis of the ellipse.

Blood oxygenators require an efficient oxygen uptake into the blood, and an equally efficient $CO_2$ removal. However, the most effective mean sparger pore size for oxygen uptake is about $1\mu$, and the most effective mean sparger pore size for $CO_2$ removal is about $40\mu$, with a wide mean variation. Heretofore, this disparity in pore sizes made it difficult to simultaneously achieve both effects in a single sparger because a gas will move along the lines of least resistance, namely along the paths adjacent the largest pores.

THE INVENTION

According to the invention, a blood oxygenator having the option of a replaceable heat exchanger is provided. The heat exchanger is of circular cross section and is produced as a hollow, integrally formed aluminum extrusion having external, spirally wound fins which are uniform and undistorted. The heat exchanger is enclosed in a container that functions as a blood reservoir and oxygenation portion in conjunction with the heat exchanger. The container is attached to a blood processing unit that removes $CO_2$ and acts as a defoamer and blood collector. The heat exchanger is removeably mounted such as with a snap-on lock and/or threaded connection to cooling and/or heating water supply outlets. Upon completion of a surgical procedure, the heat exchanger container can be easily removed from the oxygenator container and disconnected from the water supply. It is then cleaned, sterilized and reused.

A dual sparger is provided to supply both $O_2$ and $CO_2$ plus $O_2$ to the blood as it enters the spaces between the spiral fins, causing different sizes of bubbles to form, depending on the pore sizes of the two spargers. This pore size differential enables an efficient oxygen uptake and $CO_2$ removal.

DESCRIPTION OF THE PREFERRED EMBODIMENTS

Figure 1:
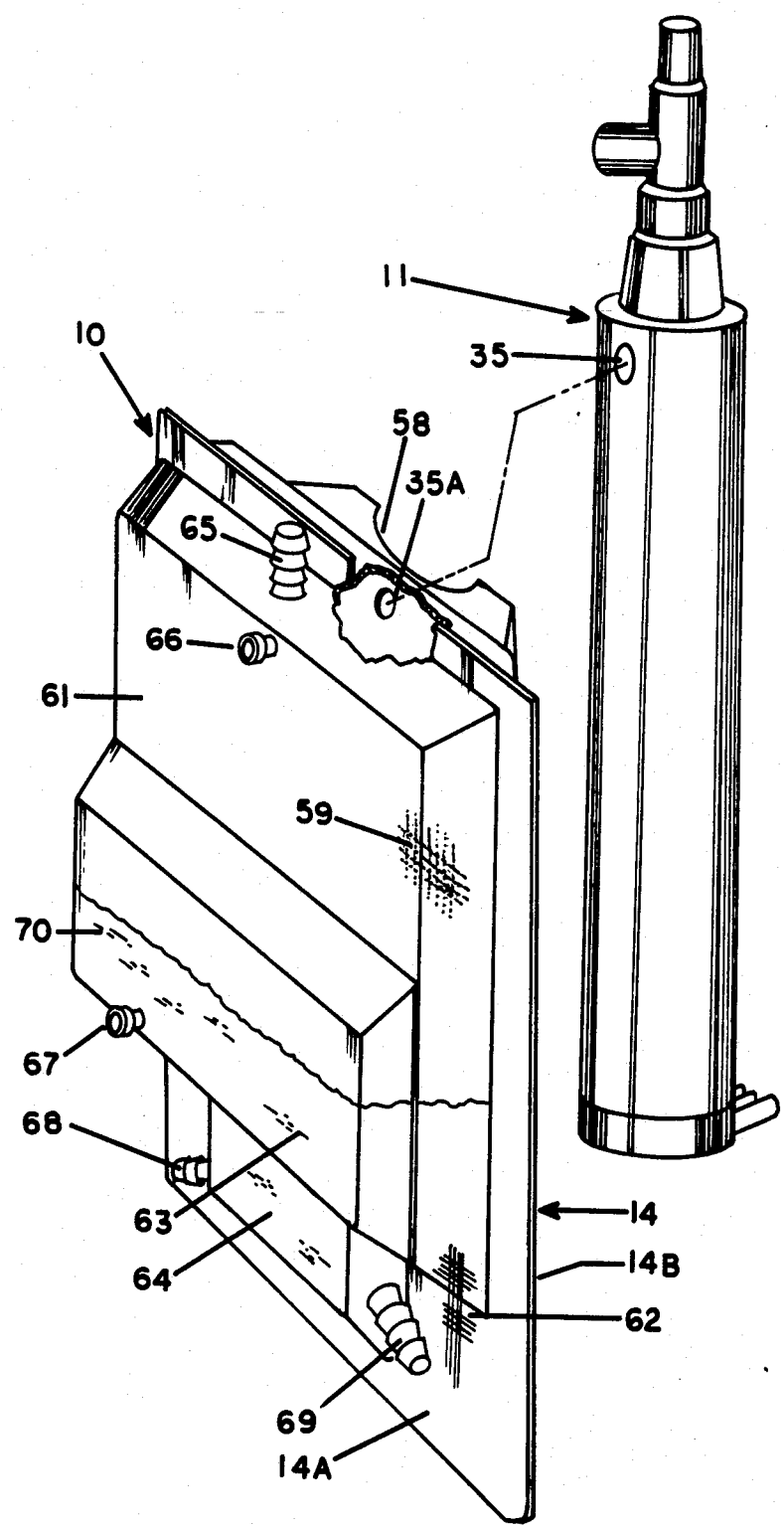
FIG. 1 is an external perspective view of the oxygenator of this invention.
Figure 2:
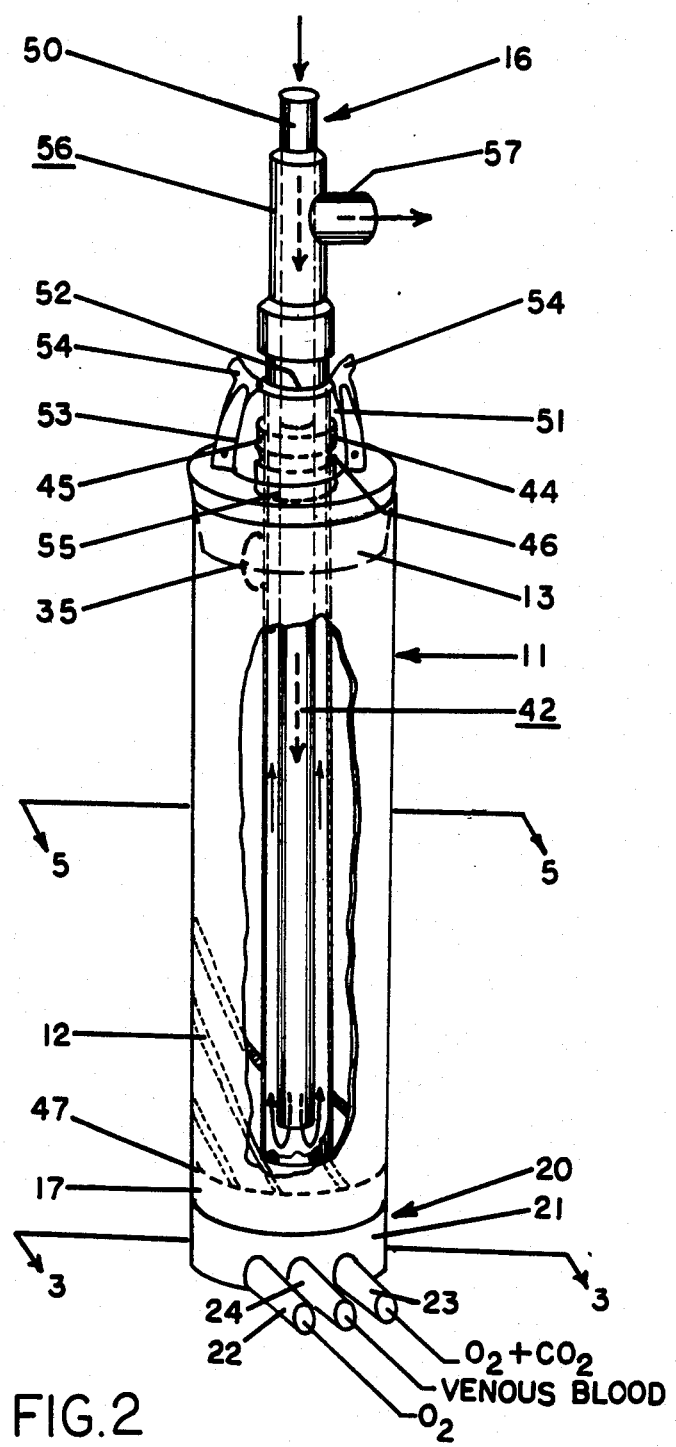
FIG. 2 is an external view, partly in perspective, of the heat exchanger of this invention and associated container.
Figure 5:
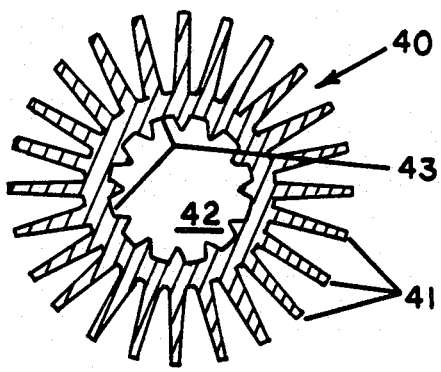
Figure 3:
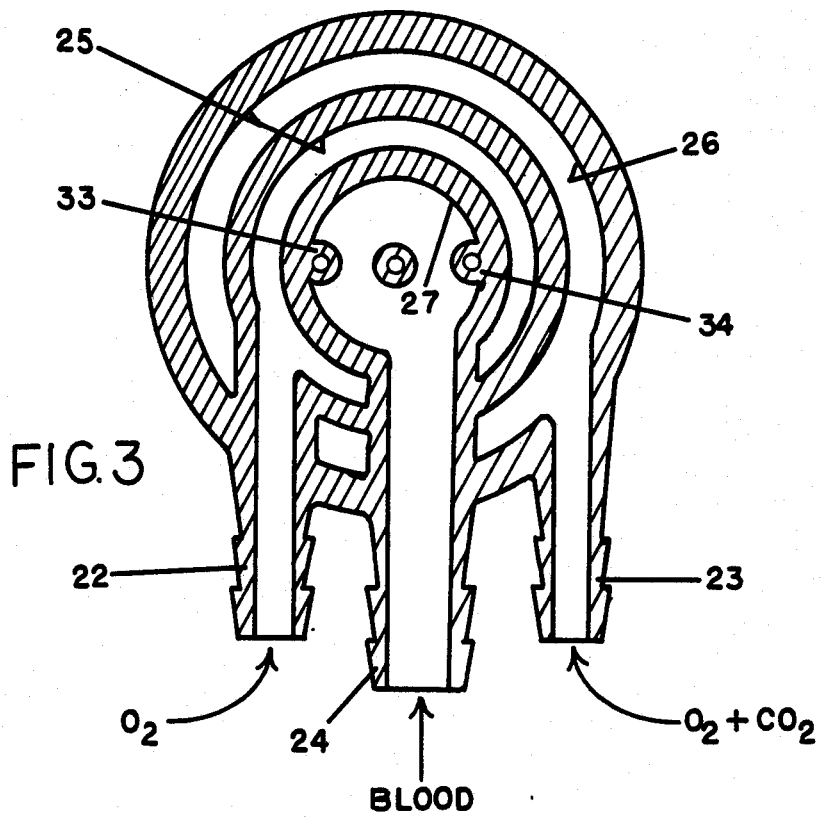
FIG. 3 is a cross section view in plan of the sparger of this invention, taken along the lines 3—3 of FIG. 2.

The blood oxygenator 10 of this invention is shown in FIGS. 1 and 2, and comprises a heat exchange container 11 into which is fitted a heat exchanger 12, the container and heat exchanger being sealed by a removeable plug 13. The container 11 is adhesively bonded to a blood processing unit 14, and is in fluid communication therewith. Oxygenation and heat exchanger takes place within the container 11 and between the fins of the heat exchanger, and the temperature controlled blood passes in a foam condition to the blood processing unit 14, where it is defoamed, degassed and is collected as liquid, oxygenated blood in a single phase.

Both the oxygenation and heat exchanger 11 and the blood processing unit 14 may be manufactured from a suitable transparent plastic such as General Electric's "LEXAN" polycarbonate resin, or a semi-transparent plastic. A water supply connection 16, that will be described, infra, is attached into the heat exchanger.

The bottom portion 17 of the container 11 is provided with a sparger 20 including a manifold 21 fed by inlets 22, 23 and 24 for $O_2$, $CO_2$ plus $O_2$, and venous blood respectively. The $O_2$ inlet 22 feeds into an inner circular outlet 25 in the manifold, while the $CO_2$ plus $O_2$ inlet 23 feeds into an outer circular outlet 26. The venous blood inlet 24 feeds tangentially into a central outlet 27; this improves gas mixing and reduces injury of blood cells due to head-on impact with the manifold walls.

Figure 4:
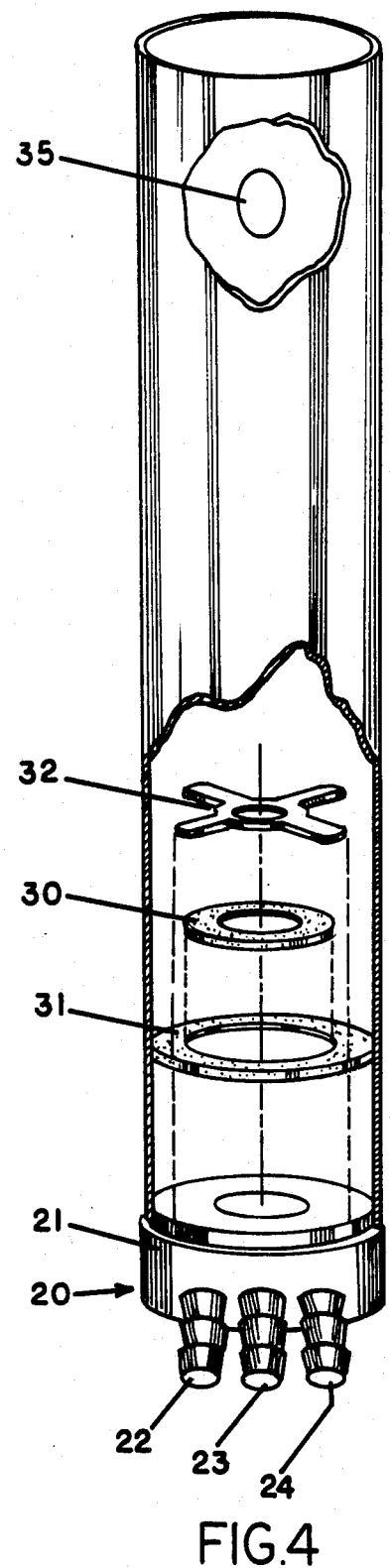
FIG. 4 is an exploded, external perspective view of the sparger components; and, FIG. 5 is an end view of the heat exchanger of this invention taken along the lines 5—5 of FIG. 2.

As shown in FIG. 4, porous, sintered rings 30, 31 of high density polyethylene, teflon, ceramic, glass beads, and the like are mounted within the outlets 25, 26 and are secured by a retainer 32 that is bolted to threaded bosses 33, 34. As indicated, the pore sizes of the rings 30, 31 are manufactured, preferably, at about $1\mu$ and $40\mu$ respectively, to produce $O_2$ and $CO_2$ plus $O_2$ bubbles, that are of the desired size. Of course, these pore sizes are preferred, not mandatory. The rings 30, 31 also enable suitable gas pressures to be developed at the outlets 25 and 26. Flow rates for the $O_2$ and $CO_2$ plus $O_2$ are about 1–6 liters/min.; the $CO_2$ content in the gas stream may vary up to 100%.

Oxygenated blood having a controlled concentration of both $O_2$ and $CO_2$ is passed along the heat exchanger and out of the container 11 as a foam through an exit port 35 (about 180° from the sparger inlets) and into the blood processing unit 14 through an entry port 35A. The blood is then defoamed, degassed and collected as whole, oxygenated blood.

The heat exchanger 12 is manufactured as an integrally formed, round aluminum extrusion having external, spirally wound fins 41. The interior of the heat exchanger defines a hollow, centrally and axially aligned chamber 42 having spirally formed fluted walls 43. A portion of the fins are machined off at the open upper end 44 to form a round, cylindrical neck 45 defining a machined, inwardly curved, locking arm engaging portion 46; the neck 45 has a length of about 4–6 inches. The bottom closed end 47 of the heat exchanger is machined flat.

Cooling or heating water is passed through the hollow chamber 42 and is directed in a spiral fashion by the fluted walls 43 to reduce turbulence. Typically, a total of about 15–24 external fins are used, each fin has an end width of about 0.045 inches, an interior width of about 0.9 inches, and is about 0.5 inches in depth. The fins have a spiral wind of about 20°–35°, and the heat exchanger length measured along the fin portion is about 11–14 inches. The overall diameter of the heat exchanger (fin-to-fin) varies from about 2 inches to 2.5 inches, the unobstructed internal diameter of the fluted, hollow chamber 42 is about 0.5–1.0 inches, and the wall thickness is about 0.15 inches. For pediatric work, the fin dimensions and overall size of the heat exchanger will, of course, be smaller. Preferably, the fins make a close fit with the interior side wall of the container. This prevents movement of blood out of an adjacent pair of fins and results in good heat exchange and oxygen transfer.

The water supply system 16 for temperature control of the heat exchanger comprises a water inlet line 50 that is threaded or otherwise attached to an open ended coupling 51 having an inlet 52, a bell shaped interior 53, and locking arms 54. An extension pipe is attached to the inlet line 50 and extends through the coupling 51. An annular space 56 is defined between the inlet 52 and the extension pipe, and the annular space feeds to an outlet pipe 57. As shown in FIG. 2, the extension pipe 55 is inserted into the heat exchanger chamber 42, and the cylindrical neck 45 of the heat exchanger is inserted into the bell-shaped interior 53 of the coupling 51. The arm engaging portion 46 of the neck coincides with the locking arms 54. Hence, when the arms are closed, as shown, the water delivery system 16 will be water tight, and will also form a strong mechanical connection with the heat exchanger. Movement of cooling water through the system is shown by the arrows. It will be appreciated that cooling (or heating) water is passed along the pipe 55 downwardly, and coaxially and centrally along the heat exchanger chamber 42 countercurrent to the flow of blood. This arrangement makes for a more efficient and uniform heat transfer. At the conclusion of a surgical procedure such as a coronary by-pass, the heat exchanger can be readily disconnected from the water supply system.

The blood processing unit 14 for oxygenated blood is shown in FIG. 1 connected (e.g. by glue bonding) to the container 11. The unit 14 is molded in two corresponding halves 14A and 14B that are edge sealed by solvent sealing or heat sealing. The unit 14 may be manufactured from a transparent plastic such as "LEXAN" polycarbonate resin or a similar material, as in the case of the container 11. The processing unit 14 has an overall oblong shape, and a central, inwardly curved portion 58 that fits with the round container 11. The capacity of the processing unit 14 is about 3–4 liters. An entry port 35A connects with the exit port 35 of the container. The upper front portion of the processing unit 14 forms an outwardly configured reservoir portion 61 where defoaming and degassing occur. Defoaming takes place by passing the blood foam through a coarse, open-cell polyurethane foam 59 and a nylon mesh (150–225 mesh) 62 that has been coated with a defoaming agent. Polyester and steel mesh also may be employed. The nylon or steel mesh is secured between the edges during sealing to accurately position the mesh and to prevent foam from leaking around the edges. If steel mesh is used, it can be heated by induction to assist in the edge sealing.

Lower reservoirs 63, 64 are provided for collecting whole blood, and these are integrally molded to the front of the blood processing unit 14. An inlet port 65 may be provided for connecting to a cardiotomy reservoir (not shown) and a $CO_2$ vent 66 is located upwardly of the degassing reservoir 61. An optional sample port 67 is located on the lower side of the reservoir 63, and outlet ports 68, 69 for oxygenated blood are positioned on the lower side of reservoir 64. For convenience, either one of the outlet ports 68, 69 may be used, depending on the orientation of the blood oxygenator relative to the patient.

During use, venous blood is fed through inlet 24 of the sparger 20 into the manifold 21, and through the central outlet 27 into the bottom of the container 11. The venous blood then moves upwardly through the container and between the spirally wound fins 21 of the heat exchanger 12. Simultaneously, water is passed through the hollow chamber 42 of the heat exchanger in the direction shown by the arrows for controlling the blood temperature, depending on the patient's condition. $O_2$ and $CO_2$ plus $O_2$ are fed through their respective inlets 22, 23 and outlets 25, 26 and rings 30, 31 to the bottom 17 of the container 11. The gases form bubbles that are absorbed by the blood as it passes upwardly between the fins and the container wall. The spiral winding of the fins enables a longer contact time to be made between the heat exchanger and blood, and also increases the oxygenation time of the blood as compared to a finned heat exchanger having only parallel fins.

As the blood reaches the upper end of the container 11, it becomes saturated with these gases, and turns foamy. This blood foam is then passed through the exit port 35 and into the blood processing unit 14 through the entry port 35A. The blood foam is broken down by the polyurethane foam 59 and mesh 62, and this causes $CO_2$ and miscellaneous gases such as $O_2$, anesthetic gases, etc., to be vented through the $CO_2$ vent 66. The defoamed, oxygenated blood 70 is collected in the reservoirs 63, 64 and returned to the patient through one of the outlets 68, 69.

At the conclusion of the operation, the heat exchanger 12 is removed from the container 11 and is disconnected from the water supply system 16. The heat exchanger is then cleaned and sterilized, after which it is ready for reuse. It will be appreciated that reassembly of the heat exchanger into a new container 11 will take place usually at the hospital, or in the operating room. Hence, production costs at the manufacturing end will be reduced. Also, since fewer heat exchangers are required, quality control can be improved with little corresponding cost increases. Furthermore, because the same few heat exchangers will be used in a facility, their individual characteristics become better known to the perfusionist.

We claim:

1. A blood oxygenator having a removeable and reuseable heat exchanger, comprising:
   (a) an elongate-shaped container providing an upper opening for insertion of the heat exchanger therein;
   (b) an elongate heat exchanger: i. formed as an integral metal extrusion; ii. defining a circular cross section; iii. providing external spiral fins; iv. including a hollow, coaxially and centrally aligned interior for circulation of heat exchange fluid therein; v. the heat exchanger being closely finned inside the container with the fins contacting the container; vi. the heat exchanger being oriented upwardly for uniform movement of blood between adjacent fins and the container to control blood temperature and oxygenate the blood; vii. the heat exchanger defining a round elongate neck at an upper end for removeable attachment to a heat exchange fluid supply, the heat exchanger being removeably insertable through the upper opening, and sealed into the container by a removeable plug surrounding the elongate neck;
   (c) a removeable plug surrounding the elongate neck;
   (d) a sparger inlet means for separately supplying $O_2$ and $CO_2 + O_2$ gas and venous blood to the container at its lower end, the sparger inlet including two separate inlet means for the $O_2$ and $CO_2 + O_2$ being positioned in proximity to the venous inlet, the $O_2$ and $CO_2 + O_2$ sparger inlets having a respective pore size differential sufficient to produce different bubble sizes from the respective spargers to enhance $O_2$ absorption and $CO_2$ removal, thereby enabling control of the oxygenator during use by varying the $CO_2$ and $O_2$ content of the gas supply; and,
   (e) a blood processing unit for defoaming, degassing and collecting oxygenated blood, the elongate container being attached to and integral with the blood processing unit, and being in fluid communication therewith through a port positioned upwardly of the container;
   whereby, the heat exchanger is insertable into the upper opening of the elongate shaped container, and sealed therein along the opening by the plug, and upon completion of use, the heat exchanger is constructed and arranged to be disengaged from the heat exchange fluid supply, and unplugged from the container, followed by cleaning, sterilization and reuse.

2. The blood oxygenator of claim 1, in which oxygenated blood foam is passed through a port in the container located upwardly of the fins, and into the blood processing unit.

3. The blood oxygenator of claim 1, in which the heat exchange fluid supply is connected to the elongate neck of the heat exchanger by a locking arm adapted to provide a quick disconnect from the heat exchanger.

4. The blood oxygenator of claim 3, in which the heat exhange fluid supply is connected to an outlet tube inserted into the hollow interior of the heat exhanger.

5. The blood oxygenator of claim 1, in which the heat exchanger has about 15–24 external fins, each fin has an end width of about 0.045 inches, an interior width of about 0.9 inches, a depth of about 0.5 inches, a spiral wind of about 20°–35°, an oxygenator length along the fins of about 11–14 inches, a fin-to-fin diameter of about 2–2.5 inches, and a diameter of the hollow interior of about 0.5–1.0 inches.

6. The blood oxygenator of claim 1, in which the porous sparger is selected from the class consisting of polypropylene, teflon, ceramic, and glass beads.

7. The blood oxygenator of claim 1, in which the container and blood processing unit are separately injection molded, and then sealed together.

8. The blood oxygenator of claim 1, providing an integrally molded inlet sparger including a manifold portion, inlets for $O_2$, $CO_2$ plus $O_2$, and venous blood into the manifold, and corresponding outlets leading from the manifold into the container, the $O_2$ sparger having a pore size of about $1\mu$, and the $CO_2$ plus $O_2$ sparger having a pore size of about $40\mu$.

9. The blood oxygenator of claim 8, in which the venous blood is supplied tangentially to the manifold.

10. The blood oxygenator of claim 1, providing a heat exchange fluid inlet supply line and a fluid outlet port line being commonly mounted within the elongate neck, and removeable therefrom, the inlet supply line defining a pipe extending into the heat exchanger through its length and adjacent to its bottom.

11. The blood exygenator of claim 1, in which the interior of the heat exchanger defines spirally fluted walls.

12. The blood oxygenator of claim 1, in which the blood processing unit includes a reservoir and a steel mesh defoaming element therebetween, the blood processing unit and reservoir being edge sealed by induction heating of the steel mesh.

13. The blood oxygenator of claim 1, in which the dual sparger inlets have pore sizes varying from about $1\mu$ for the $O_2$ inlet, to about $40\mu$ for the $CO_2 + O_2$ inlet.

14. A method for controlling a blood oxygenator having a removeable and reuseable heat exchanger, the oxygenator comprising:
   (a) an elongate-shaped container providing an upper opening for insertion of the heat exchanger therein;
   (b) an elongate heat exchanger: i. formed as an integral metal extrusion; ii. defining a circular cross section; iii. providing external spiral fins; iv. including a hollow, coaxially and centrally aligned interior for circulation of heat exchange fluid therein; v. the heat exchanger being closely finned inside the container with the fins contacting the container; vi. the heat exchanger being oriented upwardly for uniform movement of blood between adjacent fins and the container to control blood temperature and oxygenate the blood; vii. the heat exchanger defining a round elongate neck at an upper end for removeable attachment to a heat exchange fluid supply, the heat exchanger being removeably insertable through the upper opening, and sealed into the container by a removeable plug surrounding the elongate neck;
   (c) a removeable plug surrounding the elongate neck;
   (d) a sparger inlet means for separately supplying $O_2$ and $CO_2 + O_2$ gas and venous blood to the container at its lower end, the sparger inlet including two separate inlet means for the $O_2$ and $CO_2 + O_2$ being positioned in proximity to the venous inlet, the $O_2$ and $CO_2+O_2$ sparger inlets having a respective pore size differential sufficient to produce different bubble sizes from the respective spargers; and, (e) a blood processing unit for defoaming, degassing and collecting oxygenated blood, the elongate container being attached to, and integral with the blood processing unit, and being in fluid communication therewith through a port positioned upwardly of the container;

the method comprising the steps of:

inserting the heat exchanger into the upper opening of the elongate shaped container, and sealing the heat exchanger therein along the opening by means of the plug; enhancing $O_2$ absorption by the blood and $CO_2$ removal therefrom by means of the said respective pore size differential; controlling the oxygenator during use by varying the $CO_2$ and $O_2$ content of the gas supply; passing the oxygenated blood from the elongate container to the blood processing unit; defoaming, degassing and collecting oxygenated blood therein; and upon completion of use, disengaging the heat exchanger from the heat exchange fluid supply; unplugging the heat exchanger from the container; and, cleaning, sterilization and reuse.

15. The method of claim 14, in which the blood flow rates for the $O_2$ and $CO_2+O_2$ vary from about 1-6 liters.

16. The method of claim 15, in which the sparger pore sizes for the $O_2$ and $CO_2+O_2$ spargers are $1\mu$ and $40\mu$, respectively.

17. The method of claim 16, providing an integrally molded inlet sparger including a manifold portion, inlets for $O_2$, $CO_2+O_2$, and venous blood into the manifold, and corresponding outlets leading from the manifold into the container.

18. The method of claim 17, in which the venous blood is supplied tangentially to the manifold.

* * * * *